(12) United States Patent
Widlund (10) Patent No.: US 6,485,477 B2
(45) Date of Patent: Nov. 26, 2002

(54) BLANK FOR PRODUCING A SHAPED ELEMENT, THE SHAPED ELEMENT, AN ABSORBENT PRODUCT COMPRISING THE SHAPED ELEMENT, METHOD OF PRODUCING THE SHAPED ELEMENT, AND ALSO METHOD OF PRODUCING THE ABSORBENT PRODUCT

(75) Inventor: Urban Widlund, Pixbo (SE)

(73) Assignee: SCA Hygiene Products AB, Gothenburg (SE)

(*) Notice: Subject to any disclaimer, the term of this patent is extended or adjusted under 35 U.S.C. 154(b) by 24 days.

(21) Appl. No.: 09/759,463

(22) Filed: Jan. 16, 2001

(65) Prior Publication Data

US 2001/0001313 A1 May 17, 2001

Related U.S. Application Data

(62) Division of application No. 09/335,723, filed on Jun. 18, 1999.

(30) Foreign Application Priority Data

Jun. 18, 1998 (SE) ............................................. 9802176

(51) Int. Cl.⁷ ................................................. A61F 13/15
(52) U.S. Cl. .................. 604/385.01; 604/386; 156/62.6
(58) Field of Search ...................... 604/385.01, 385.03, 604/385.04, 385.201, 386, 387; 156/62.6, 250, 251, 308.4

(56) References Cited

U.S. PATENT DOCUMENTS

| | | | | |
|---|---|---|---|---|
| 84,703 A | * | 12/1868 | Moore | |
| 2,043,325 A | * | 6/1936 | Jackson | 128/284 |
| 2,591,079 A | * | 4/1952 | Leaton | 128/284 |
| 3,570,492 A | * | 3/1971 | Bettencourt | 128/290 |
| 3,575,174 A | | 4/1971 | Mogor | 128/290 |
| 3,738,362 A | * | 6/1973 | Sneider | 128/280 |
| 3,834,389 A | * | 9/1974 | Dulle | 128/285 |
| 3,863,637 A | * | 2/1975 | MacDonald et al. | 128/287 |
| 4,182,334 A | * | 1/1980 | Johnson | 128/287 |
| 4,327,732 A | * | 5/1982 | Thinnes | 128/290 |
| 4,605,404 A | * | 8/1986 | Sneider | 604/385 R |
| 4,642,110 A | * | 2/1987 | Dudek | 604/385.1 |
| 4,673,403 A | | 6/1987 | Lassen et al. | 604/385 R |
| 4,946,454 A | * | 8/1990 | Schmidt | 604/385.1 |
| 5,171,302 A | | 12/1992 | Buell | 604/385.1 |
| 5,514,104 A | | 5/1996 | Cole et al. | 604/366 |
| 5,690,625 A | | 11/1997 | Widlund | 604/385.1 |
| 6,156,951 A | * | 12/2000 | Gustafsson et al. | 604/369 |
| 6,160,197 A | * | 12/2000 | Lassen et al. | 604/358 |
| 6,171,291 B1 | * | 1/2001 | Osborn, III et al. | 604/385.1 |
| 6,203,654 B1 | * | 3/2001 | McFall et al. | 156/268 |
| 6,210,385 B1 | * | 4/2001 | Mizutani | 604/385.01 |

FOREIGN PATENT DOCUMENTS

| | | | | |
|---|---|---|---|---|
| EP | 0136524 | 4/1985 | ........... | A61F/13/18 |
| EP | 0850628 | 7/1998 | ........... | A61F/13/15 |
| FR | 2463610 | 2/1981 | ........... | A61F/13/00 |

* cited by examiner

*Primary Examiner*—John G. Weiss
*Assistant Examiner*—Michael G. Bogart
(74) *Attorney, Agent, or Firm*—Young & Thompson (57) ABSTRACT

The invention relates to a blank intended to constitute a shaped element in an absorbent product, such as a sanitary towel, an incontinence pad or a panty liner, which blank is made from a rigid material and initially has a plane and essentially elongate shape with a longitudinal direction and a transverse direction, two short sides and two long sides, two end portions and a central portion, one end portion being wider than the central portion and having a width which increases towards the short side of the blank and the other end portion having a cutout. The invention also relates to a shaped element produced from the blank, an absorbent product comprising such a shaped element, and also methods of producing a shaped element and an absorbent product comprising the shaped element.

4 Claims, 11 Drawing Sheets

BLANK FOR PRODUCING A SHAPED ELEMENT, THE SHAPED ELEMENT, AN ABSORBENT PRODUCT COMPRISING THE SHAPED ELEMENT, METHOD OF PRODUCING THE SHAPED ELEMENT, AND ALSO METHOD OF PRODUCING THE ABSORBENT PRODUCT

CROSS REFERENCE TO RELATED APPLICATIONS

This application is a division of application Ser. No. 09/335,723, filed Jun. 18, 1999, the contents of which are hereby incorporated by reference.

TECHNICAL FIELD

The invention relates to a blank intended for producing a shaped element in an absorbent product, such as a sanitary towel, an incontinence pad or panty liner, which blank is made from a rigid material and initially has a plane and essentially elongate shape with a longitudinal direction and a transverse direction, two short sides and two long sides, a central portion and two end portions.

The invention also relates to a shaped element for an absorbent product, such as a sanitary towel, an incontinence pad or panty liner, which shaped element is made from a rigid material and has an essentially elongate shape with a longitudinal direction and a transverse direction, two short sides and two long sides, a central portion and two end portions, one end portion of which has a bowl-shaped portion.

The invention also relates to an absorbent product, such as a sanitary towel, an incontinence pad or a panty liner, which product has an essentially elongate shape with two end portions and a central portion located between the end portions, and a longitudinal center line, which product comprises a shaped element and which product has a bowl-shaped portion in one end portion and a ridge-like raised portion in the other end portion.

The invention also includes a method of producing a shaped element according to the above, and also a method of producing an absorbent product, such as a sanitary towel, an incontinence pad or a panty liner.

BACKGROUND

Conventional absorbent products of the type referred to above usually have a plane shape. As the genital area of women does not have a correspondingly plane appearance, problems can therefore arise in fitting and wearing such products. The bearing of the product against the body is not the best that could be desired and if looseness occurs there is also a great risk of leakage.

In order to solve this problem, it has been proposed that the absorbent products should be of bowl-shaped design rather than plane. Broadly speaking, this shape fits better against the contours of the body. A bowl-shaped contour can be achieved by, for example, fitting elastic to the product. EP 155 515 describes how an absorbent product is imparted a bowl-shaped appearance by elastic being fitted in the longitudinal side edges of the product. WO 96/20679 describes an absorbent product which comprises a resilient component and tensioning members in order to give the product a bowl-shaped appearance.

A problem with products of the abovementioned type is that they do not fit particularly well against the anatomy of the wearer but simply have a generally bowl-shaped appearance. Such a shaped product therefore does not have a good fit against the body.

Furthermore, gaps tend to occur between the body of the wearer and the panties of the wearer because many women wear panties of inferior quality, either from the outset or as a result of great age, during their menstruation. When neither the absorbent product nor the panties are capable of maintaining good contact with the body of the wearer, the risk of leakage of menstrual fluid past both the absorbent product and the panties becomes great.

EP 302 523 describes an absorbent product which has a three-dimensionally designed, anatomically adapted shape. The product has an end portion of flat or concave design and an end portion which is provided with a raised portion. The flat or concave end portion is intended to be placed in front of the mons pubis of the wearer and the end portion comprising the raised portion is intended to fit against the buttocks of the wearer. The three-dimensional design of the product is obtained by folding a moderately rigid absorption body. In order to make the raised portion permanent, the rear side of the product is provided with a glued surface in the end portion that is to have the raised portion. When the raised portion has been created, it is preserved with the aid of the glue. One problem with a product of this type is that it tends to collapse under the pressure from the body of the wearer. Another problem is that the glued sealing of the raised portion loses its adhesion and the product is then flattened out.

In order to solve this problem, it has been proposed that products are provided with dimensionally stable, rigid members. Such products are described in SE-A-9604223-9 and SE-A-9604221-3. The members, or shaped elements, which bring about the dimensional stability are three-dimensionally designed members made from material which resists crumpling and flattening when it is subjected to forces from the body of the wearer, for example when the wearer walks or sits on the product.

A problem which is just as great as that constituted by plane absorbent products when they are to be adapted to the three-dimensional anatomy of the wearer is that constituted by the three-dimensional absorbent in the production process. Three-dimensional parts are difficult to handle in a production process, for example when they are to be joined together to form an absorbent product.

OBJECT OF THE INVENTION

An object of the invention is to remedy the abovementioned problems and produce a shaped element for absorbent products which is easy to produce and also an absorbent product comprising the shaped element, which product is leakproof, comfortable and easy to produce.

BRIEF DESCRIPTION OF THE INVENTION

A blank of the type referred to in the introduction, in which problems associated with previously known such products have essentially been removed, is according to the invention characterized in that one end portion on the blank is wider than the central portion and has a width which increases towards the short side of the blank and the other end portion has an elongate cutout, or slit.

According to an embodiment of the invention, the widest part on the end portion is 1.5–5 times as wide as the narrowest width on the central portion.

According to another embodiment, the shaped element has been joined together to form a raised portion in one end portion, from a plane blank, and the bowl-shaped portion has been created with the aid of a fold indication extending in the transverse direction of the shaped element. Additional fold indications, can be arranged essentially in the longitudinal direction of the blank, in at least the central portion of the blank, on each side of a longitudinal center line through the blank.

The invention also includes an absorbent product which is characterized in that a ridge-like raised portion in one end portion of the product has been created by the shaped element being joined together to form a raised portion from a plane blank, and in that a bowl-shaped portion has been created with the aid of a fold indication extending in the transverse direction of the shaped element.

According to an alternative embodiment, the absorbent product has leakage barriers arranged on both sides of the longitudinal center line.

The invention also includes a method of producing a shaped element, which is characterized in that a blank intended to constitute the shaped element is produced in plane form with an essentially elongate shape with a longitudinal direction and a transverse direction, two short sides and two long sides, two end portions and a central portion, where one end portion is given a width which increases towards the short side of the blank and the other end portion is provided with a cutout, the blank is folded double along a longitudinal center line of the blank so that two surfaces are formed on the blank, the cutout is joined together and the joined parts are folded up into a three-dimensional state.

According to the invention, the fold indications can be arranged in the longitudinal direction of the blank before the cutout is joined together.

The invention also includes a method of producing an absorbent product, according to which a blank intended to constitute a shaped element in the absorbent product is produced in plane form with an essentially elongate shape with a longitudinal direction and a transverse direction, two short sides and two long sides, two end portions and a central portion, where one end portion is given a width which increases towards the short side of the blank and the other end portion is provided with a cutout, the blank is folded double along a longitudinal center line of the blank so that two surfaces are formed on the blank, an absorption layer and then an outer layer are arranged on each surface, after which the side edges along the cutout formed, the absorption layers and also the outer layers are joined and the joined parts are folded out into a plane state.

According to an alternative embodiment of the method of producing the absorbent product, two fold indications are arranged essentially in the longitudinal direction of the blank, in at least the central portion of the blank, one on each side of the longitudinal center line.

DESCRIPTION OF THE INVENTION

The abovementioned problems are solved by the present invention. This is brought about by a blank for a shaped element being produced from a plane piece of rigid material. The blank is clipped, punched or cut out from the piece of material so that it has an essentially elongate shape with two long sides and two short sides, two end portions and a central portion. One end portion has a width which is considerably greater than the width at the narrowest part of the blank, which is the central portion. The other end portion has a longitudinal slit or cutout in the longitudinal direction of the blank. The cutout is arranged along a longitudinal center line extending through the blank. The longitudinal center line is in this connection an imaginary line which divides the blank into two preferably symmetrical parts of the same size. The center line is arranged in the longitudinal direction of the blank at the same distance from its two long sides. The slit or cutout is arranged in such a manner that, in the part where the cutout is arranged, the blank assumes a shape with two elongate parts which diverge in relation to the longitudinal center line.

The intention of arranging a shaped element in an absorbent product is to be able to impart to the product a three-dimensional shape which is retained and possibly also accentuated during use of the product. Materials suitable for producing the blank for the shaped element must have adequate bending and torsional rigidity in order to resist deformation during use. Polyethylene or polypropylene laminates with a layer thickness of at least 0.4 mm can be mentioned as examples of plastic materials which have been found to have adequate bending rigidity and torsional rigidity to achieve the necessary dimensional stability. The material rigidity of a plastic film which is suitable for use as a shaped element in a product according to the invention should exceed 100 N, measured according to ASTM D 4032-82 "Circular Bend Procedure", which method is described in detail in EP 336 578. In this connection, material rigidity means the bending rigidity of a plane material layer.

After the blank has been cut out, it is folded double along the longitudinal center line and along the cutout. In this state, the cutout is joined together. This is done by, for example, welding or gluing. The shaped element has thus been formed. That is to say, when the blank has been cut out and joined together so that it needs only to be folded up in order for it to assume a three-dimensional shape, it is referred to as a shaped element.

In this plane state, the shaped element can be packed and supplied to the user who can then herself make an absorbent product by providing the shaped element with absorption layers and if appropriate outer layers. In this way, a reusable shaped element can be produced, something which is economically advantageous. The user can replace absorption layers and outer layers but use the shaped element a number of times.

Many users, however, attach great importance to convenience and prefer to buy ready-made absorbent products. After the blank has been joined together along the cutout to form a finished shaped element, the shaped element is provided, while still in a folded plane state, with an absorption layer and an outer layer on each side. The absorption layer and the outer layer are joined together by means of, for example, welding or gluing. Alternatively, outer and absorption layers are arranged on the blank before the cutout is joined together and the cutout, the absorption layers and the outer layers are joined in one and the same step. A further alternative for joining the absorbent product together is that the blank is folded and the cutout is joined together so that the shaped element is prepared. Then a continuous absorption layer is folded around the shaped element while it is still folded together, after which a continuous outer layer is folded in the same way around the folded-together shaped element. In this way, a complete absorbent product is obtained without the outer and absorption layers having to be joined together from two parts each.

In conventional products, a liquid-impermeable layer is joined to the rear side of the absorption layer and the product, which is that side of the product which is intended to face towards the undergarments of the wearer during use, that is to say away from the wearer. This is so as to protect the undergarments of the wearer against any leakage of fluid through the whole product. With an absorbent product according to the invention, no such extra liquid-impermeable layer is necessary. As the shaped element is usually made of liquid-impermeable material, the shaped element constitutes the liquid-impermeable rear side. A product according to the invention is thus simpler in this way also than conventionally constructed absorbent products.

The entire production of the absorbent product has been carried out in plane form and the production process for a dimensionally stable, three-dimensional product has thus been simplified considerably in relation to production processes in which a shaped element is moulded, as in, for example, SE,A, 9604224-7.

When an absorbent product according to the invention, comprising a shaped element according to the invention, is folded up into its use state, it will fit well against the anatomy of the wearer. The end portions and the central portion on the blank or shaped element do not constitute three delimiting parts of the same size of the blank or shaped element but are indicated in order to describe the three different appearances the blank has in the longitudinal direction. One end portion, the front end portion, is intended to face forwards on the user when used in a sanitary towel. Forwards on the wearer means that the short side of the end portion will be that part of the towel which faces towards the abdomen of the wearer. The front end portion has a bowl-shaped portion. When a sanitary towel comprising a shaped element according to the invention is positioned with the bowl-shaped end portion forwards on the wearer, said portion will surround the mons pubis of the wearer. The other end portion, the rear end portion, is intended to face backwards on the wearer during use. Backwards on the wearer means that the short side of the end portion will be that part of the towel which faces towards the back of the wearer. The rear end portion has a ridge-like raised portion. When a sanitary towel comprising the shaped element according to the invention is positioned with the ridge-like end portion backwards on the wearer, that is to say towards the bottom region of the wearer, the product will naturally fit against the anatomy of the wearer and will therefore also bear closely against the body by itself.

The central portion on the shaped element has a raised portion. When a sanitary towel comprising a shaped element according to the invention is positioned against the body of the wearer, the raised portion on the central portion will fit against the vestibule of the wearer. The raised portions in the central portion and the end portion can constitute a continuous raised portion. The central portion and the rear end portion have been folded up so that they have ridge-like raised portions on the upper side of the shaped element. A fold indication can be arranged on the front end portion in order to facilitate the end portion being folded up and turned inside out so that the end portion assumes a bowl-shape on the upper side. Such a fold indication can consist of perforations or of a material weakening produced by, for example, cold or hot stamping. On turning inside out, the bowl-shaped portion is folded up towards the upper side on the shaped element so that the portion forms an angle with the other parts of the shaped element, seen from one long side of the shaped element. The angling and the bowl-shape together result in the shaped element fitting well against the mons pubis of a prospective wearer. The upper side on the shaped element is in this respect the side which is intended to face towards the wearer during use. The rear side on the shaped element is the side which is intended to face away from the wearer during use. In a corresponding manner to a complete absorbent product, the front end portion on the shaped element is the end portion which is intended to face forwards on the wearer during use, that is to say the end portion which is intended to face towards the abdomen of the wearer. The rear end portion on the shaped element is then the end portion which is intended to face backwards on the wearer during use, that is to say the end portion which is intended to face towards the back of the wearer.

In order further to improve an absorbent product according to the invention, comprising a shaped element according to the invention, the shaped element can be provided with one or more longitudinal fold indications. These fold indications contribute to shaping the shaped element and thus the absorbent product according to the anatomy of the wearer. Another purpose of the fold indications is to create channels in the shaped element and thus leakage barriers in the finished product. As the shaped element and the finished product have ridge-like raised portions in the central portion and one end portion, there is a risk of fluid running down the inclined side surfaces of the raised portions and on out past the side edges of the product, leading to side leakage. Leakage barriers moulded in a dimensionally stable shell for an absorbent product having ridge-like raised portions are described in SE,A, 9702398-0. Such leakage barriers mean, however, that the shaped element has a three-dimensional shape throughout the entire production process of the absorbent product.

According to the present invention, the fold indications are arranged in the shaped element before it is joined together with the outer layer and the absorption layer to form the absorbent product. It is also possible to arrange the fold indications after joining together. In this way, the shaped element has a plane shape throughout, broadly speaking, the entire production process of the absorbent product. Fold indications can be produced in a number of different ways. For example, the fold indications can consist of stampings or weakenings in the material, such as grooves or the like produced by means of small wheels or rollers. Alternatively, the fold indications can be produced by compression moulding. It is also possible to fold the finished product in the desired manner and make the folds permanent by heating or pressing.

Fold indications which serve as side leakage barriers on each side of the ridge-like raised portions in the central portion and the end portion are advantageously arranged in the longitudinal direction of the shaped element, starting from the longitudinal center line where it intersects a transverse fold line made in the front end portion in order to create the bowl-shape in this portion. From this starting point, a fold line is arranged on each side of the longitudinal center line and on both sides of the raised portions in the central portion and the end portion. The fold lines consist of straight lines which diverge from the center line so that channels are formed in the shaped element on the central portion and relatively large parts of the end portion. The fold lines stop a few centimetres from the short side of the product in the end portion which has the raised portion.

The fold lines do not have to be straight but can, for example, bend away towards the long sides of the shaped element. This results in a product with a further improved body shape. Another way of obtaining leakage barriers and increased adaptation of the absorbent product to the body is to arrange a number of fold lines on each side of the longitudinal center line and on both sides of the raised portions in the central portion and the end portion. For example, two or three fold lines can be arranged on each side of the center line. Extra lines, in addition to one on each side of the longitudinal center line, can start from the same point as the two first fold lines. That is to say from an imaginary intersection point between the longitudinal center line and the transverse fold line which makes the bowl-shape of the end portion possible. From this starting point, they diverge further from the longitudinal center line. Additional lines can also be arranged parallel to the two original fold lines. All the fold lines described are arranged at a distance of at least several millimetres from the long sides of the shaped element in order to create channels and consequently leakage barriers in the finished absorbent product.

In order to obtain better adaptation of the absorbent product to the body, additional fold lines can be arranged on the shaped element. For example, arc-shaped fold lines, which are concave towards the longitudinal center line, can be arranged on each side of the longitudinal center line in the end portion which has the raised portion. That is to say arc-shaped fold lines are arranged around the raised portion. Such fold lines can of course also be arranged in the central portion or otherwise common lines running through both the central portion and the end portion can be arranged.

In order to obtain a further improved adaptation to the body of the end portion against the mons pubis of the wearer, that end portion of the product which is to form the bowl-shaped portion in the shaped element can also be cut out with a cutout. In this way, greater rounding of the bowl can be obtained. The production process is of course more complicated because two cutouts are to be joined together before the shaped element can be folded up into its final shape.

The invention also includes an absorbent product which comprises the shaped element according to the invention. The designations used for the product and for the shaped element apply similarly for the absorbent product also. For example, the front end portion on the blank is intended to constitute the front end portion on the shaped element which is arranged in the front end portion on the absorbent product.

An absorbent product comprising a shaped element according to the invention does not require any fastening arrangement such as glued surfaces on the rear side of the product. A product according to the invention stays in place naturally by means of its anatomical design. Such products are described in SE,A, 9604222-1 and SE,A,9604224-7. The decisive factor with regard to whether the product stays in place by itself is the rigidity of the shaped element and the design of the shaped element. The end portion which is intended to face forwards on the wearer during use is to be wider than the central portion. It is also an advantage if the other end portion is somewhat wider than the central portion but this is not crucial for fastening. Preferably, the widest part on the front end portion is 1.5–5 times as wide as the smallest width on the central portion.

In order that the shaped element and thus the product will not cause discomfort for the wearer and possibly leakage, it is important that the cross section or width of the central portion is adapted according to the anatomy of the wearer. The most critical area in the crotch region of the wearer from the point of view of comfort as far as the width of the product is concerned is where the muscle group passes which has its origin on the inside of the pelvic diaphragm and its attachment along the thigh. This muscle group consists of the adductor brevis, adductor longus, gracilis and adductor magnus muscles.

Measurements have shown that the distance in the crotch region of the wearer between the adductor muscle groups on the left side and the right side is surprisingly alike for all people and is around 30 mm. Fatness of course influences the width between the thighs but the width between the muscle groups in the crotch region is the same and it is this width which determines whether a product may feel as if it rubs. The fat tissue settles on the outside of the muscles but does not contribute to any feeling of discomfort. If the product is constructed from a very rigid material, the width of the central portion should therefore not exceed 35 mm, at least in the area which is to fit between the muscle groups. This critical area is approximately 5–15 mm long in the longitudinal direction of the product.

A product according to the invention, which stays in place without any special fastening arrangements, comprises a shaped element made of a rigid material, which shaped element comprises a front end portion which is 1.5–5 times as wide in its widest portion as its central portion is in its narrowest portion. The rear end portion is advantageously also wider than the central portion so as to avoid the absorbent product "wandering" in any direction.

The central portion on the shaped element is 35 mm or narrower, within at least an area of the central portion which is 5–15 mm long. The front end portion is wider on that part of the end portion which faces towards the front short side of the product, that is to say the side which is intended to face forwards on the wearer during use, than on the part which faces towards the central portion. The front end portion can have, for example, a triangular shape. The front end portion is 52.5–175 mm wide at its widest. The front end portion is advantageously also shaped so that it has an angle in relation to the other parts of the shaped element, seen from one long side of the shaped element.

BRIEF DESCRIPTION OF THE FIGURES

The invention will be described in greater detail below with reference to the exemplary embodiments shown in the drawings, in which.

DETAILED DESCRIPTION OF THE FIGURES AND EMBODIMENTS

Figure 1:
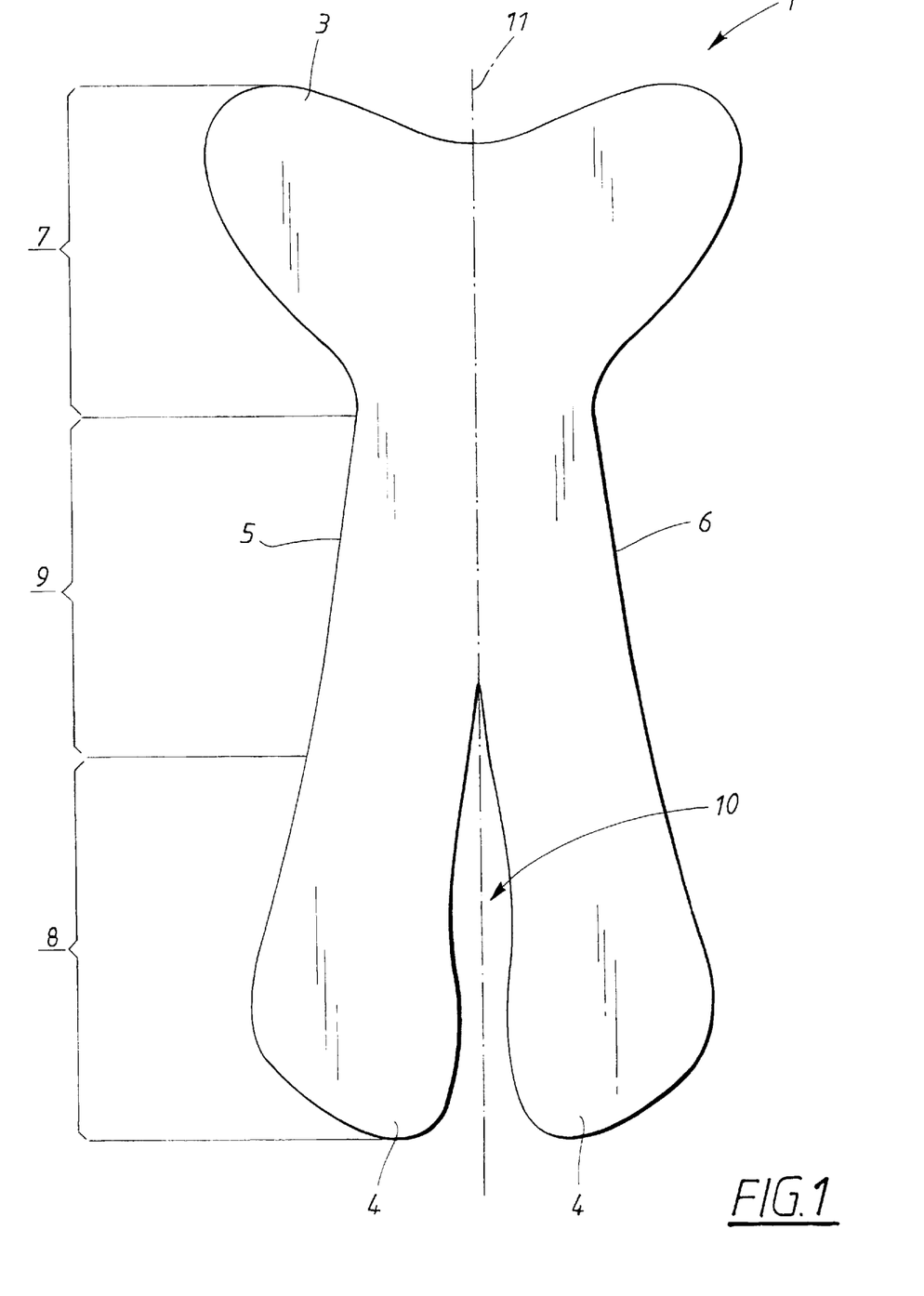
FIG. 1 shows a blank according to the invention.
Figure 2:
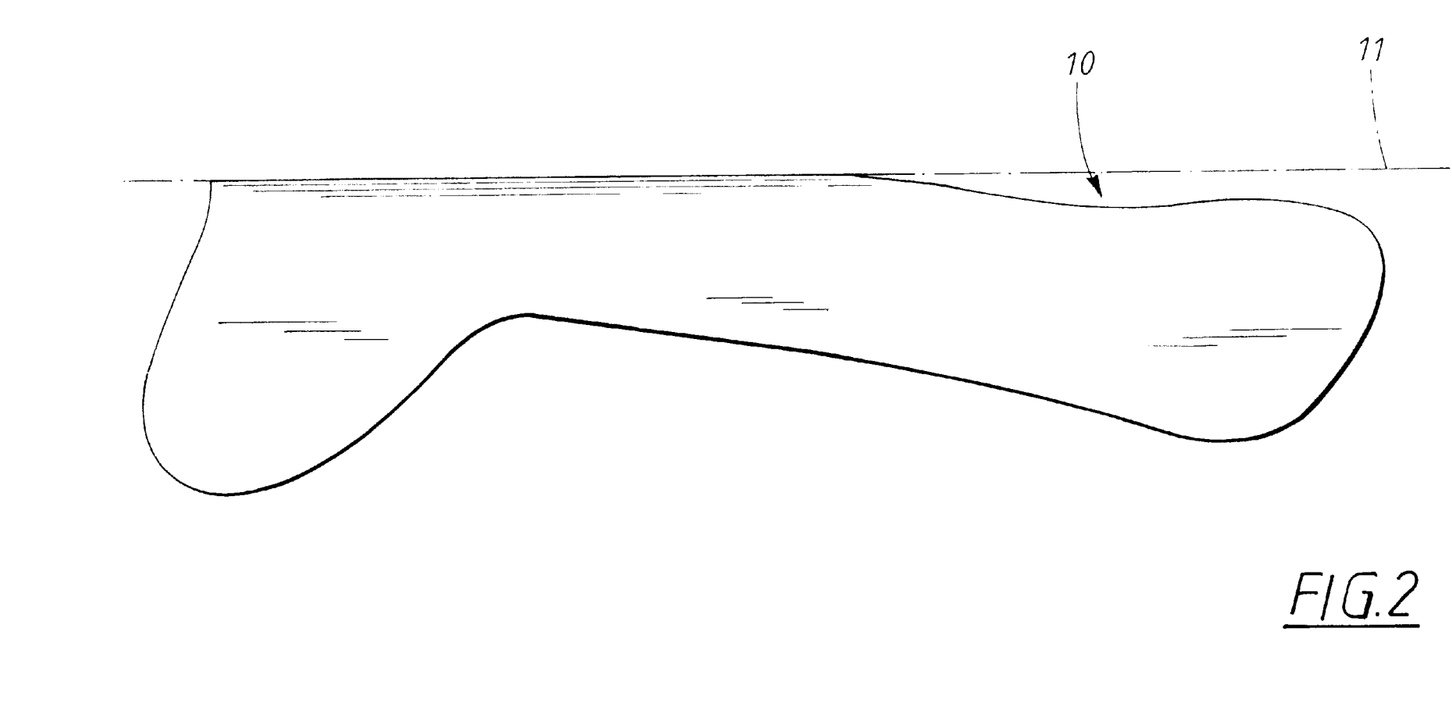
FIG. 2 shows a blank according to the invention folded double, viewed from one of its long sides.
Figure 3:
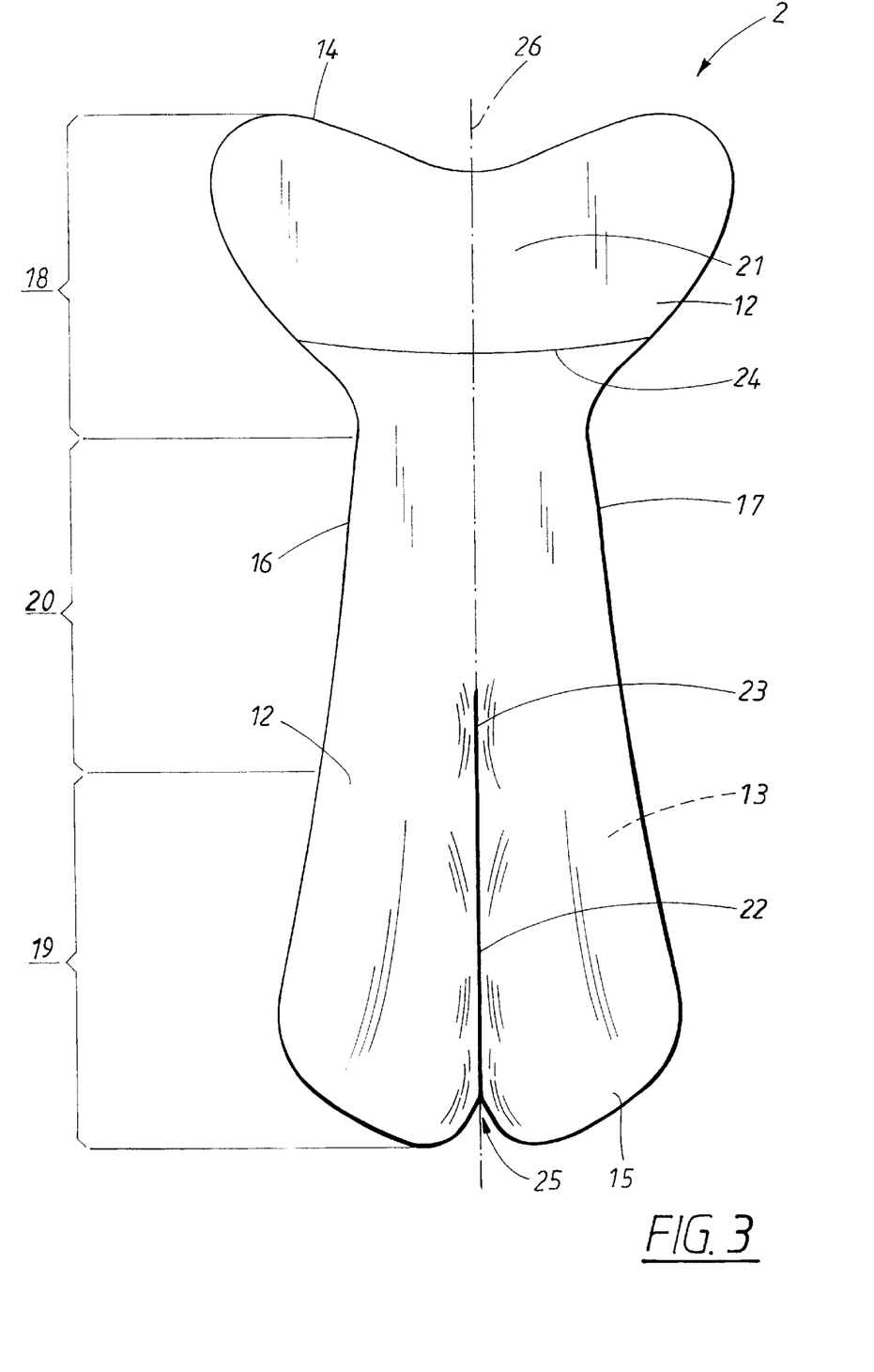
FIG. 3 shows a shaped element according to the invention.
Figure 4:
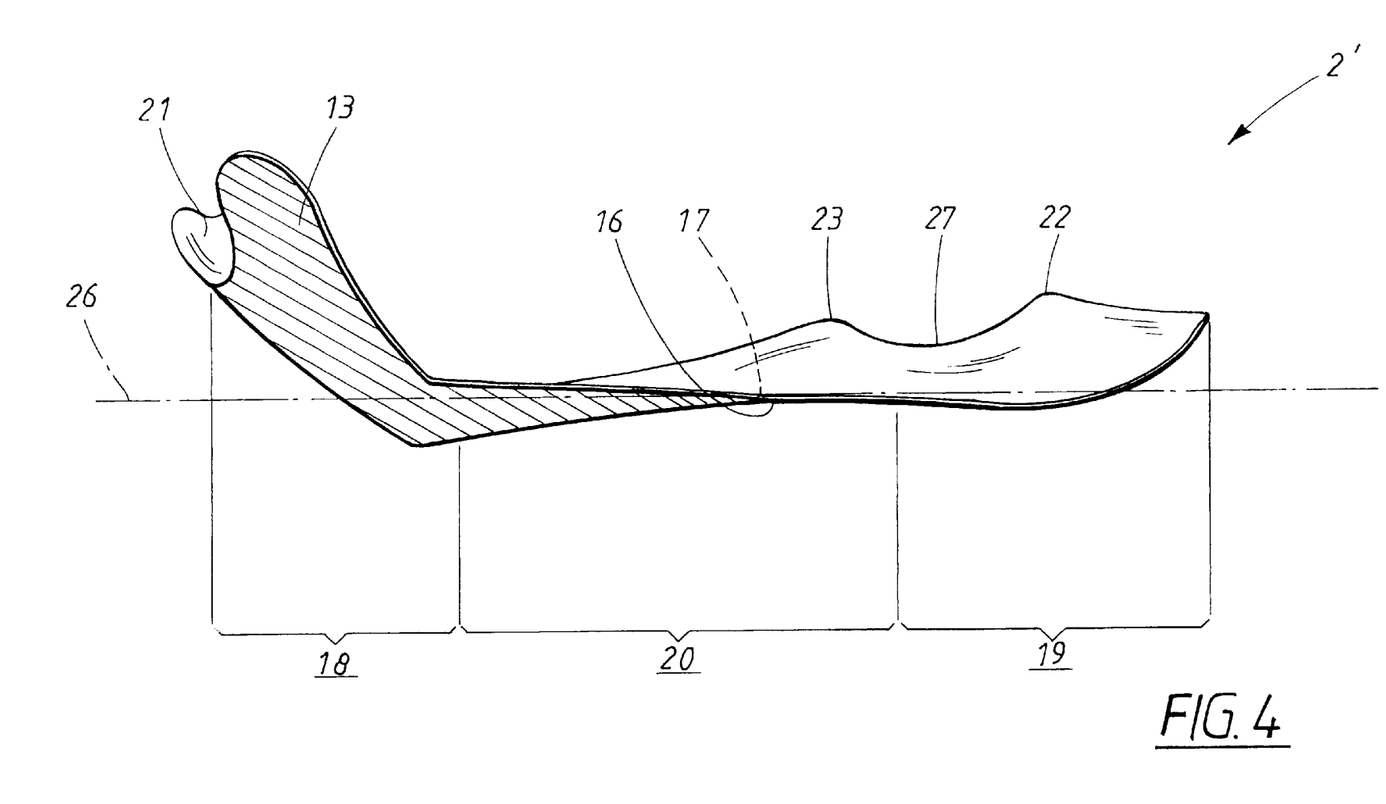
FIG. 4 shows a shaped element according to the invention, viewed from one of the long sides of the shaped element.

FIGS. 1 and 2 show a blank 1 for a shaped element intended to be positioned in an absorbent product such as a sanitary towel, an incontinence pad or a panty liner. The blank 1 is the description of the shaped element before it has been joined together to create its final three-dimensional shape. FIGS. 3 and 4 show the shaped element 2 as it appears when it is positioned in an absorbent product.

The blank 1 shown in FIG. 1 has a plane and essentially elongate shape with a longitudinal direction and a transverse direction, two short sides 3, 4 and two long sides 5, 6, two end portions 7, 8 and a central portion 9. One end portion 7 has a width which increases towards the short side 3 of the blank and the other end portion 8 has a cutout 10. The cutout 10 is arranged along the longitudinal center line 11 of the blank. The longitudinal center line 11 of the blank means an imaginary line which is located in the longitudinal direction of the blank, at the same distance from the two long sides 5, 6 of the blank.

FIG. 2 shows the blank 1 seen from one 5 of its long sides. The blank 1 has been folded double along its longitudinal center line 11, that is to say along the cutout 10. In this state, the cutout 10 is joined together. This is carried out by, for example, welding or gluing. The shaped element 2 has thus been formed.

The shaped element 2 shown in FIG. 3 has a three-dimensional and essentially elongate shape with a longitudinal direction and a transverse direction, an upper side 12 and a lower side 13, two short sides 14, 15 and two long sides 16, 17, two end portions 18, 19 and a central portion 20. The end portions 18, 19 and the central portion 20 do not constitute three delimiting parts of the same size of the blank but are indicated in order to describe the three different appearances the shaped element has in the longitudinal direction.

One end portion, the front end portion 18, is intended to face forwards on the wearer when used in a sanitary towel. Forwards on the wearer means that the short side 14 of the end portion will be that part of the towel which faces towards the abdomen of the wearer. The front end portion 18 has a bowl-shaped portion 21. When a sanitary towel comprising a shaped element 2 according to the invention is positioned with the bowl-shaped end portion 21 forwards on the wearer, said portion will surround the mons pubis of the wearer.

The other end portion, the rear end portion 19, is intended to face backwards on the wearer during use. Backwards on the wearer means that the short side 15 of the end portion will be that part of the shaped element and thus of the towel which faces towards the back of the wearer. The rear end portion 19 has a ridge-like raised portion 22. When a sanitary towel comprising the shaped element 2 according to the invention is positioned with the rear end portion 19 backwards on the wearer, that is to say towards the bottom region of the wearer, the product will naturally fit against the anatomy of the wearer and will therefore also bear closely against the body by itself.

The central portion 20 on the shaped element 2 has a raised portion 23. When a sanitary towel comprising a shaped element 2 according to the invention is positioned against the body of the wearer, the raised portion 23 on the central portion 20 will fit against the vestibule of the wearer.

FIG. 3 shows the shaped element 2 folded up or folded apart, that is to say with the front portion angled upwards and also with the central portion and the rear portion folded out, the position the shaped element is in when it is used in an absorbent product. A fold indication 24 has been arranged on the front end portion 18 and the end portion 18 has been folded up and turned inside out so that the end portion 18 has a bowl-shaped portion 21 on its upper side 12. The fold indication 24 shown is not critical in order to bring about the folding up of the front end portion 18 but simply constitutes an advantageous means of facilitating such folding. The central portion 20 and the rear end portion 19 have been folded up so that they have ridge-like raised portions 22, 23 on the upper side 12 of the shaped element. On turning inside out, the bowl-shaped portion 21 is folded up towards the upper side 12 on the shaped element 2 so that the portion 21 forms an angle with the other parts of the shaped element, seen from one long side 16 of the shaped element. The angling and the bowl-shape together result in the shaped element 2 fitting well against the mons pubis of a prospective wearer. The upper side 12 on the shaped element 2 is that side on the shaped element which is intended to face towards the wearer during use. The lower side 13 on the shaped element 2 is the side which is intended to face away from the wearer during use. As mentioned above, the front end portion 18 on the shaped element 2 is the end portion which is intended to face forwards on the wearer during use, that is to say the end portion which is intended to face towards the mons pubis of the wearer. The rear end portion 19 on the shaped element 2 is, therefore, the end portion which is intended to face backwards on the wearer during use, that is to say the end portion which is intended to face towards the buttocks of the wearer.

The rear end portion 19 on the shaped element 2 in FIG. 3 has on the short side 15 a small, wedge-shaped cutout 25, arranged symmetrically about a longitudinal center line 26 of the shaped element 2. A longitudinal center line of the shaped element means an imaginary line extending in the longitudinal direction of the shaped element, which line divides the shaped element into two essentially symmetrical parts of the same size. The cutout 25 has a triangular shape. The purpose of the cutout 25 is to increase adaptation to the body and comfort for the wearer.

FIG. 4 shows the shaped element 2 seen from one 16 of its long sides. The three-dimensional shape of the shaped element is clear here. The lower side 13 on the shaped element 2 is hatched. The front end portion 18 of the shaped element has a bowl-shaped portion 21 which forms an angle in relation to the longitudinal center line 26 of the shaped element 2 and to the central portion 20 and rear end portion 19 of the shaped element. The central portion 20 of the shaped element has a raised portion 23 intended to fit against the vestibule of the wearer during use. The rear end portion 19 also has a raised portion 22 intended to fit against the buttocks of the wearer. The two raised portions 22, 23 constitute a continuous raised portion in relation to the long sides 16, 17 of the shaped element. However, as can be seen in the figure, there is a valley-shaped portion 27 half-way between the raised portion 23 on the central portion 20 and the raised portion 22 on the rear end portion 19. The valley-shaped portion 27 is to fit against the perineum of the wearer during use. It is possible for the raised portions 22, 23 of the central portion and the end portion to constitute a single continuous raised portion rising gradually towards the rear end portion. Such a raised portion does not display the same adaptation to the body of the wearer but is easier to produce. Some users also experience discomfort from sanitary towels which are very well adapted to the body, as a result of which there may be cause for this reason also to employ a simpler construction of the raised portions 22, 23.

Figure 5:
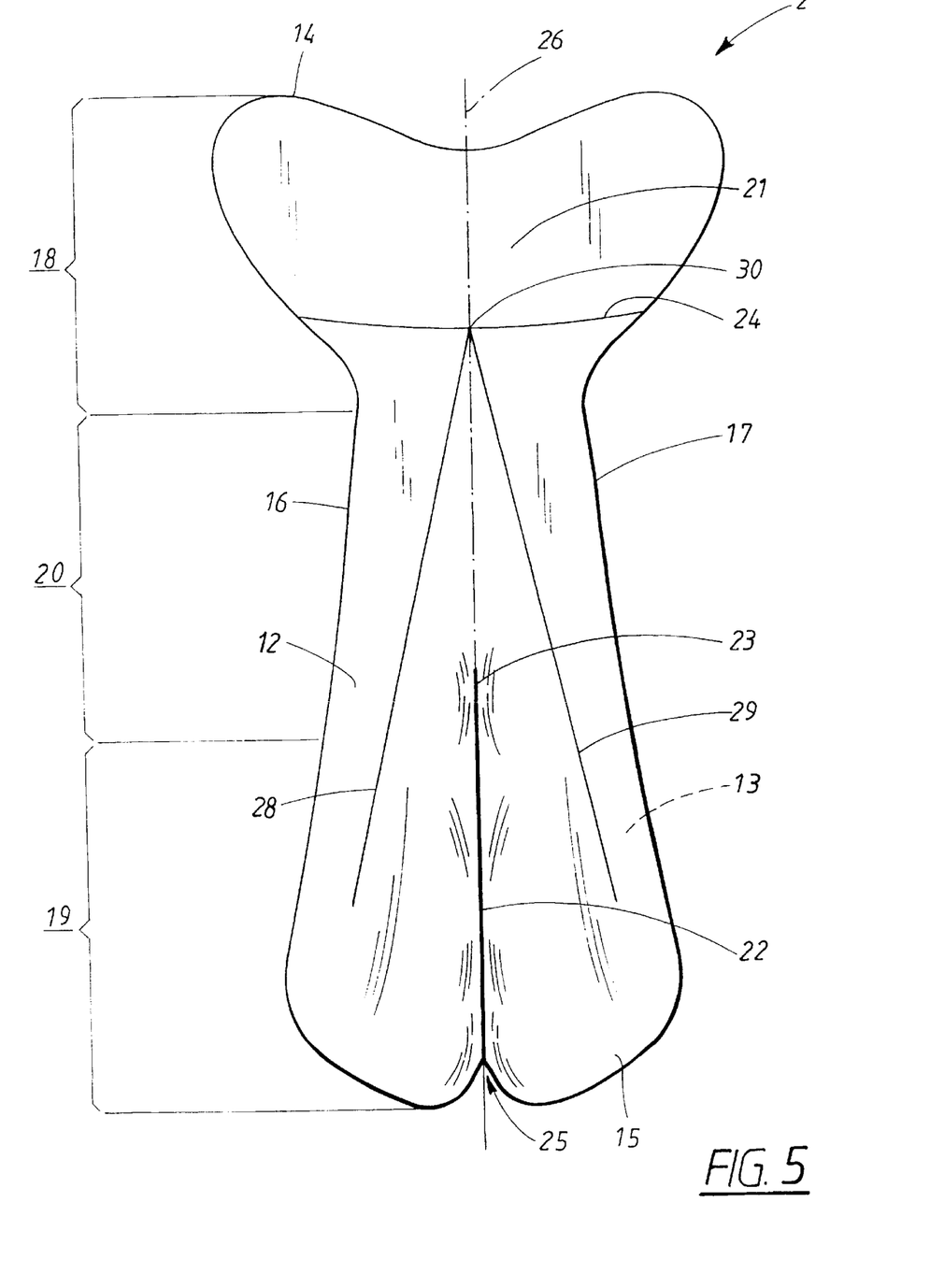
FIG. 5 shows a shaped element according to an embodiment of the invention.

FIG. 5 shows a shaped element 2 according to a further embodiment of the invention. The shaped element 2 according to FIG. 5 has all the characteristics which the shaped element 2 in FIG. 3 has. The shaped element 2 has a fold indication 24 in the front end portion 18, arranged in the transverse direction of the shaped element. Two additional fold indications, or fold lines, 28, 29 are arranged essentially in the longitudinal direction of the shaped element. These two fold lines 28, 29 have their starting point at the point 30 where the longitudinal center line 26 of the shaped element intersects the transverse fold line 24 in the front end portion 18. From this point, the fold lines 28, 29 run in a diverging manner, one on each side of the longitudinal center line 26. Alternatively, for example in embodiments where the transverse fold line has been omitted, the fold lines 28, 29 can diverge from a point located slightly further back or further forward on the shaped element. Longitudinal fold lines 28, 29 can thus be arranged so that they start from the narrowest portion of the shaped element. It is also possible to arrange fold lines which do not run together at a point but are arranged at a distance from one another at their front ends also.

The fold lines 28, 29 shown in FIG. 5 run rectilinearly through the entire central portion 20 on each side of the raised portion 23 and stop at the transition between the central portion 20 and the rear end portion 19. Alternatively, it is of course possible to make the fold lines 28, 29 shorter or longer than those shown in FIG. 5.

Figure 6:
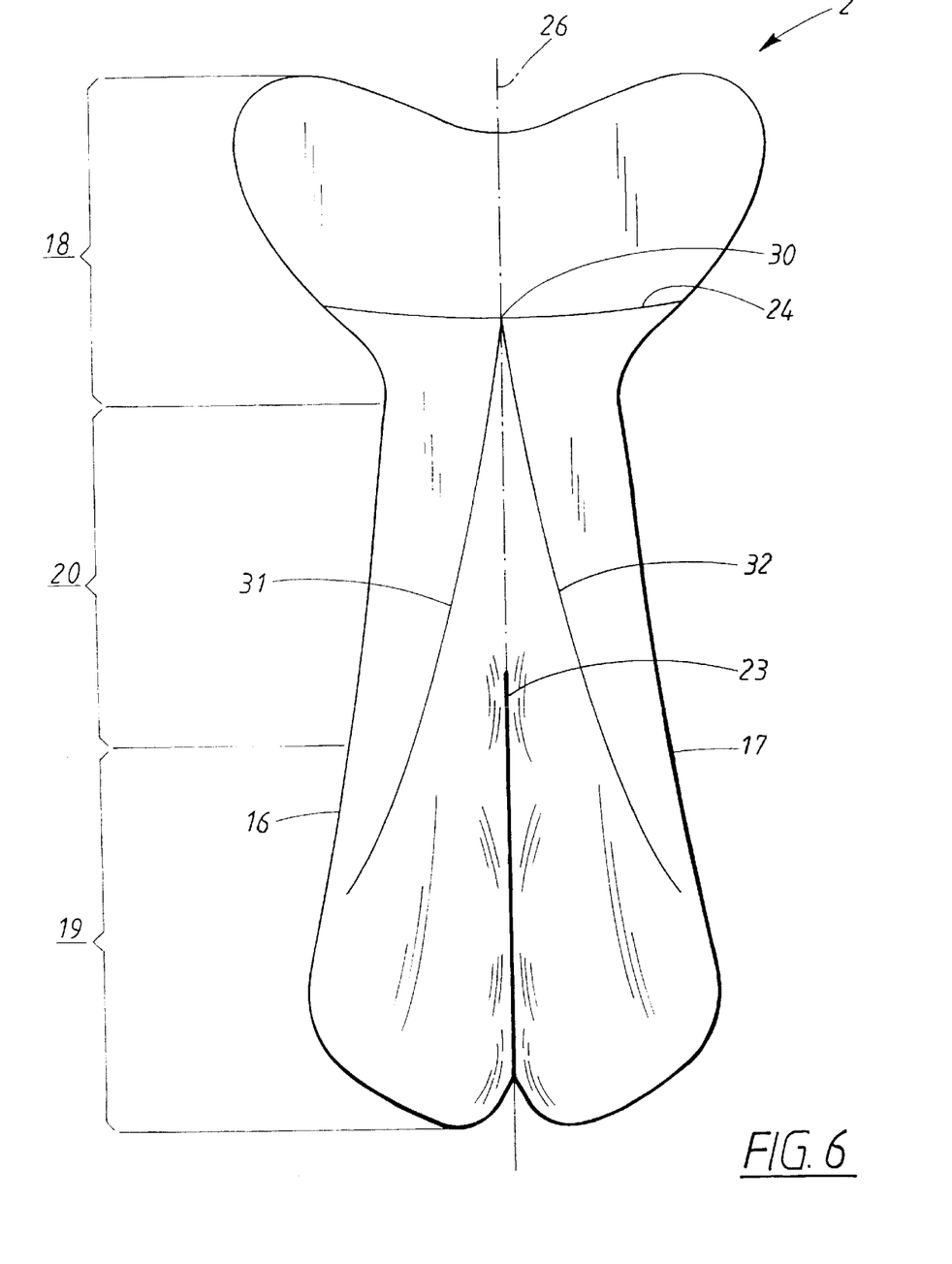
FIG. 6 shows a shaped element according to an alternative embodiment of the invention.

As FIG. 6 shows, fold lines 31, 32 on both sides of the raised portion 23 can be arranged in lines which are not straight, essentially arranged in the longitudinal direction of the shaped element. The fold lines 31, 32 in FIG. 6 start from the intersection point 30 between the longitudinal center line 26 of the shaped element and the transverse fold line 24 in the front end portion 18. From this point 30, the two fold lines 31, 32 run in an arc-shaped manner, one on each side of the longitudinal center line 26, through the central portion 20 of the shaped element, to terminate in the rear end portion 19 of the shaped element a few millimetres from the long sides 16, 17 of the shaped element. The fold lines 31, 32 diverge from the longitudinal center line 26.

Figure 7:
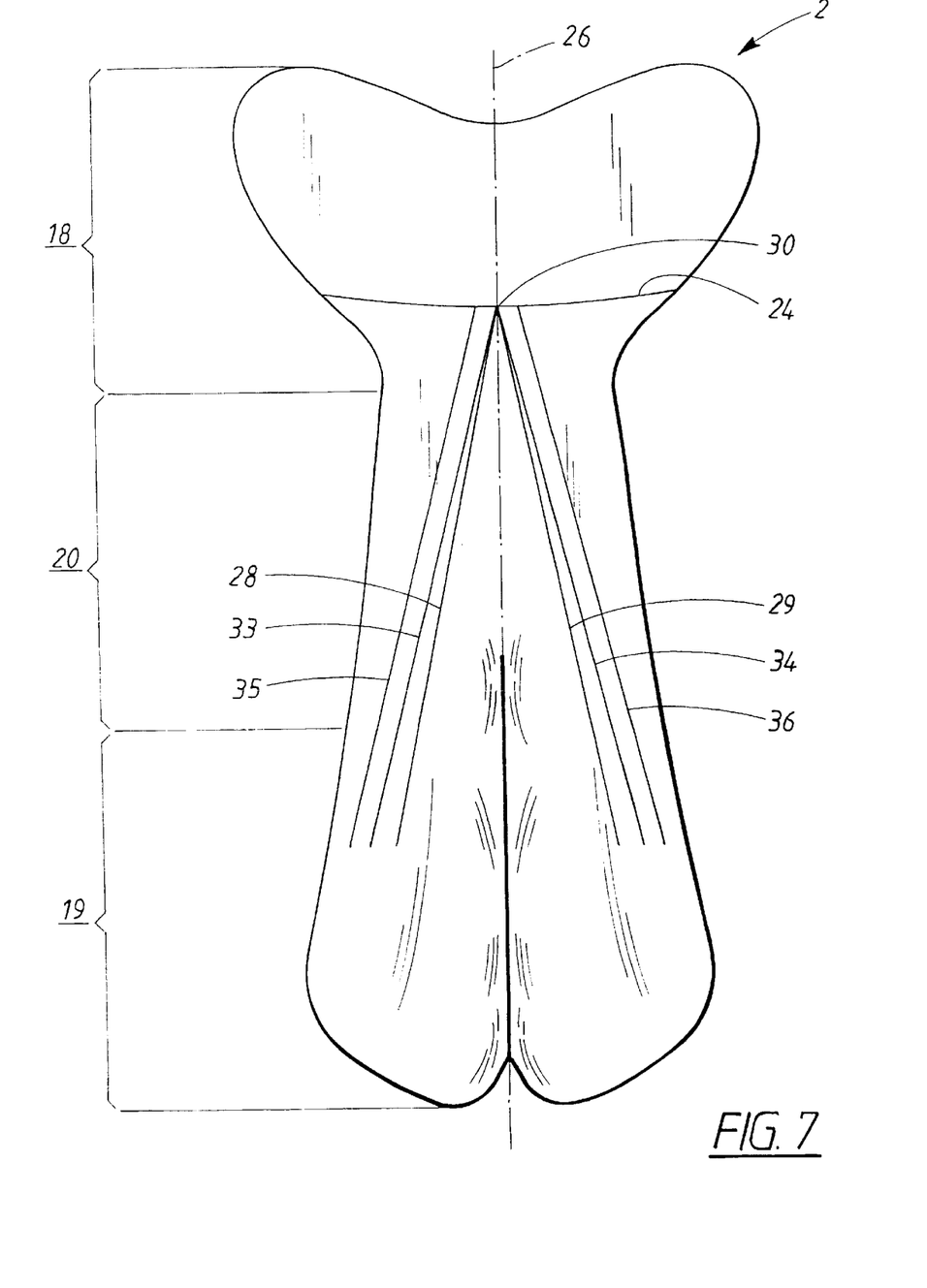
FIG. 7 shows a shaped element according to a further embodiment of the invention.

FIG. 7 shows a further alternative embodiment of the invention. This figure shows a shaped element 2 which has, in addition to two rectilinear fold lines 28, 29 arranged essentially in the longitudinal direction of the shaped element, four extra fold lines 33–36 arranged in the longitudinal direction. That is to say, the shaped element 2 has six longitudinal fold lines 28–36, three on each side of the longitudinal center line 26. These fold lines 33–36 are also rectilinear and two run on each side of the longitudinal center line 26. Two of the additional fold lines 33, 34 start from the same starting point as the original two fold lines 28, 29, namely the intersection point 30 between the longitudinal center line 26 and the transverse fold line 24 in the front end portion 18. The two lines 33, 34 then run outside the original two 28, 29 in the same manner as these. That is to say they diverge from the center line 26 while running through the central portion 20 of the shaped element towards its rear end portion 19. The two additional fold lines 33, 34 are arranged one on either side of the center line 26, outside the original fold lines 28, 29, seen from the center line 26. Arranged outside the additional fold lines 33, 34 are another two fold lines 35, 36, one on each side of the longitudinal center line 26. These fold lines 35, 36 are arranged parallel to the two fold lines 33, 34 lying closest to them. Consequently, they do not start from the same points as each other or the other fold lines 28, 29, 33, 34.

Figure 8:
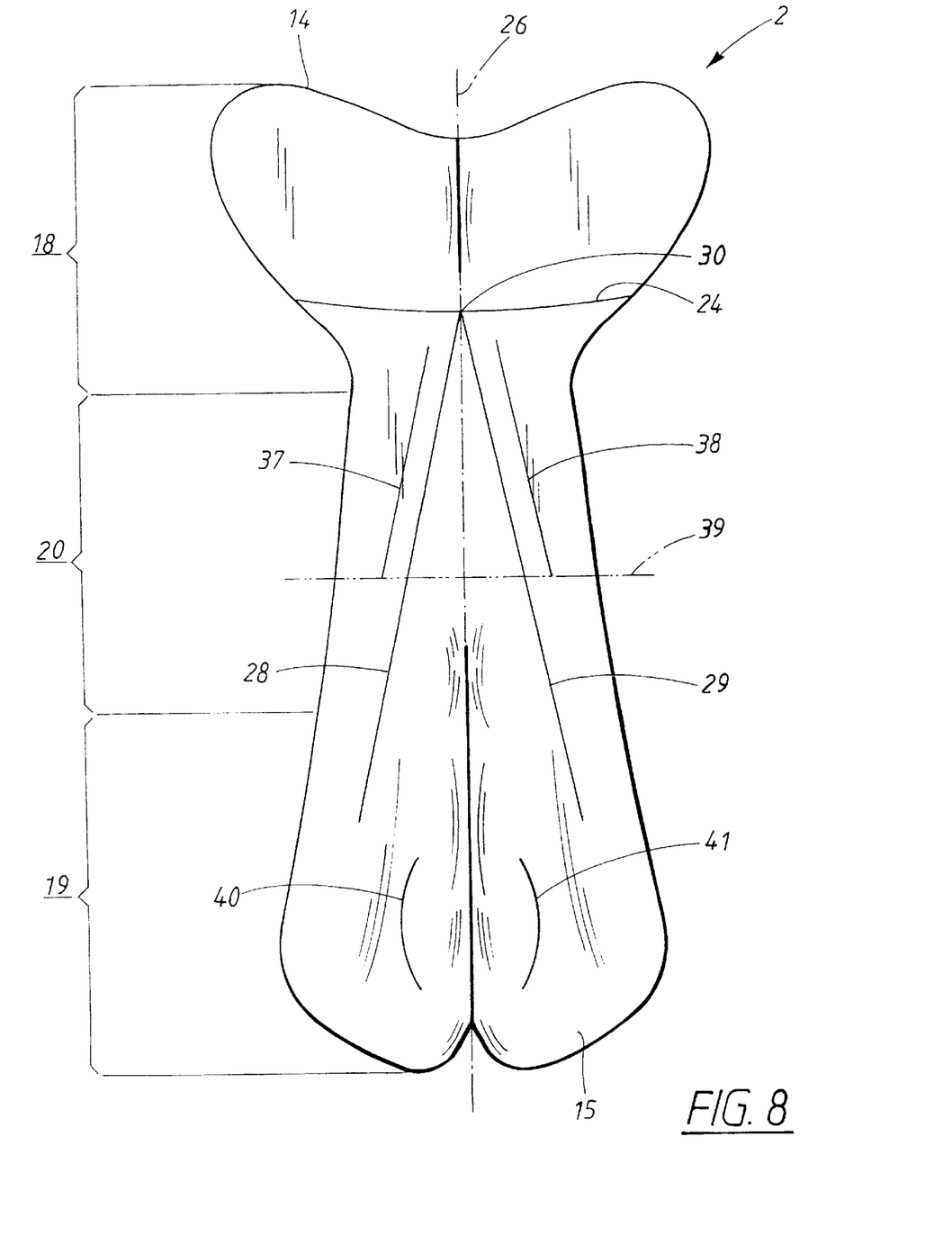
FIG. 8 shows a shaped element according to yet another embodiment of the invention.

FIG. 8 shows a shaped element 2 according to yet another embodiment of the invention. As in the preceding figures, the shaped element 2 has a transverse fold line 24 arranged in the front end portion 18 of the shaped element and also two fold lines 28, 29 arranged essentially in the longitudinal direction of the shaped element. The two longitudinal fold lines 28, 29 start from the intersection point 30 between the longitudinal center line 26 and the transverse fold line 24. From this point 30, the fold lines 28, 29 diverge from the longitudinal center line 26 as they run through the shaped element 2. The longitudinal fold lines 28, 29 stop at the transition between the central portion 20 and the rear end portion 19.

In addition to the fold lines 28, 29 indicated, the shaped element also has, according to FIG. 8, two fold lines 37, 38 arranged essentially parallel to the original longitudinal fold lines 28, 29 and outside these in relation to the center line 26. These additional fold lines 37, 38 are considerably shorter than the orignal fold lines 28, 29 lying inside them and run between the transition between the front end portion 18 and the central portion 20 and an imaginary transverse center line 39 of the shaped element 2. A transverse center line 39 is a line arranged in the transverse direction of the shaped element at the same distance from the two short sides 14, 15 of the shaped element. Fold lines 40, 41 are also arranged in the rear end portion 19 of the shaped element. These fold lines 40, 41 are arranged symmetrically and in an arc-shaped manner along the longitudinal center line 26 of the shaped element. The fold lines 40, 41 are thus arranged in a convex manner around the longitudinal center line 26.

Figure 9:
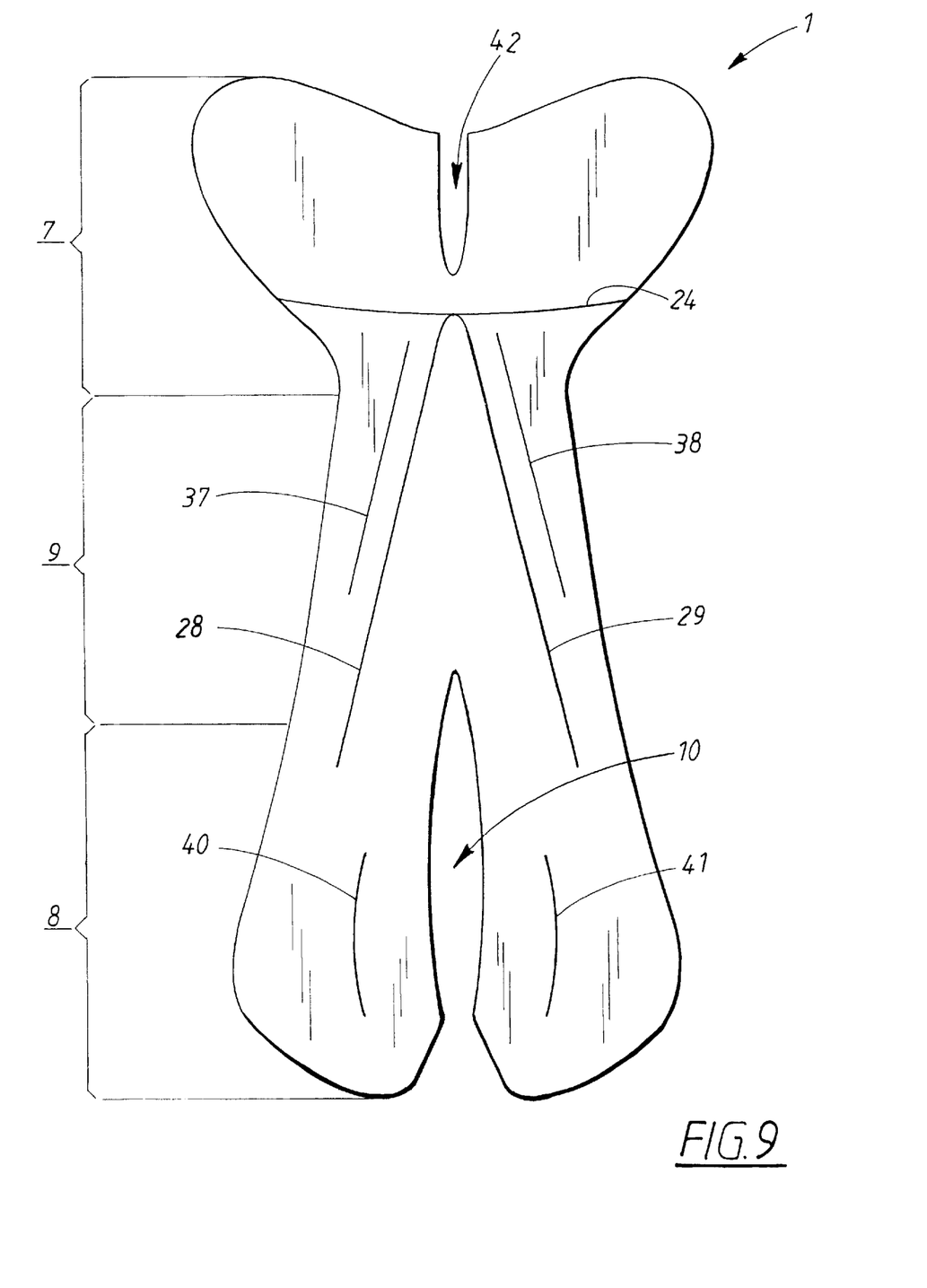
FIG. 9 shows the blank for the shaped element in FIG. 8.

FIG. 9 shows a blank 1 for the shaped element 2 in FIG. 8. The blank 1 has the fold lines described above in connection with FIG. 8. That is to say the fold lines 24, 28, 29, 37, 38, 40, 41 have been made before the joining together of the blank 1. As an alternative to this, the fold lines 24, 28, 29, 37, 38, 40, 41 can be arranged after the blank 1 has been joined together to form the shaped element 2. The blank 1 has a cutout 42 in the front end portion 7. This cutout 42 is joined together after the blank 1 has been folded in the same way as the cutout 10 in the rear end portion 9. Arranging a cutout 42 in the front end portion 7 also of course complicates the production process but makes possible even better adaptation to the body. The bowl-shaped portion in the shaped element formed can in this way be adapted better to the mons pubis of the wearer.

Figure 10:
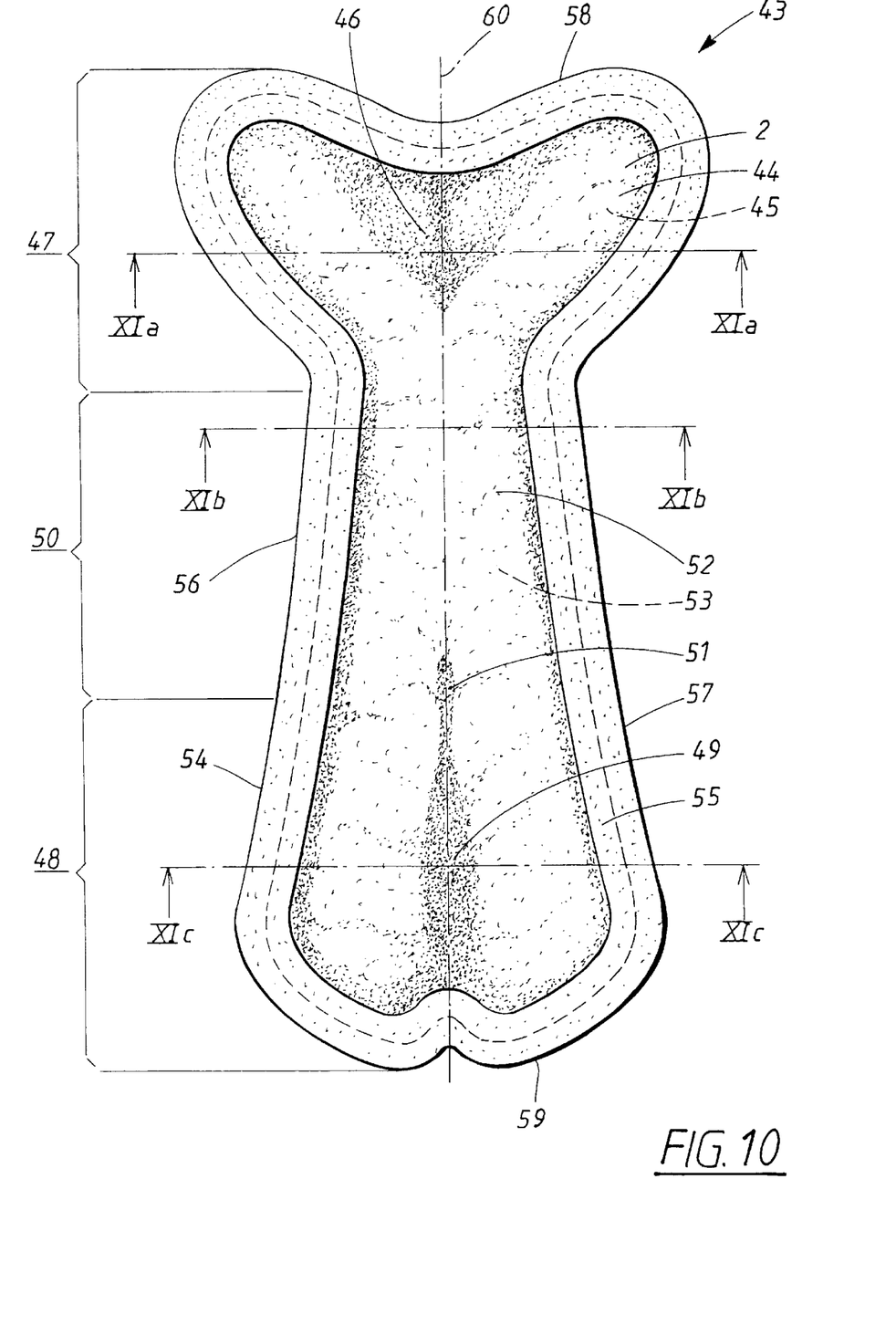
FIG. 10 shows a sanitary towel according to the invention.

FIG. 10 shows a sanitary towel 43 comprising a shaped element 2 according to the invention. The sanitary towel 43 has an upper side 44 and a lower side 45, the upper side 44 being liquid-permeable and the lower side 45 being liquid-impermeable. The liquid-permeable upper side 44 on the sanitary towel 43 is intended to face towards the body of the wearer during use and the liquid-impermeable lower side 45 is intended to face away from the body of the wearer during use. Liquid-permeability and liquid-impermeability are achieved in conventional sanitary towels by each side 44, 45 being provided with layers which are liquid-permeable and liquid-impermeable respectively. On the sanitary towel 43 according to the invention, there is no separate liquid-impermeable layer but the shaped element 2 is made from a liquid-impermeable material and thus constitutes the liquid-impermeable rear side on the sanitary towel 43. The upper side 44 on the sanitary towel 43 has a bowl-shaped portion 46 in one end portion 47 and a ridge-like raised portion 49 in the other end portion 48. The central portion 50 has a ridge-like raised portion 51 on the upper side 44 of the sanitary towel.

The sanitary towel 43 in FIG. 10 has a liquid-permeable outer layer 52 arranged on that side of the sanitary towel 43 which is intended to face towards the wearer during use. An absorption layer 53 is arranged immediately inside the outer layer 52. The shaped element 2 is arranged adjacent to the other side of the absorption layer. The layers 52, 53, 2 are joined together with one another, for example by gluing or ultrasonic welding.

The material in the outer layer 52 can be, for example, a perforated plastic film, a netting made of plastic or textile material, a non-woven or a laminate made of, for example, a perforated plastic layer and a non-woven layer. The plastic may be a thermoplastic, such as polyethylene. The non-woven material may be made of natural fibres, such as cellulose or cotton, or synthetic fibres, such as polyethylene, polypropylene, polyester, polyurethane, nylon or regenerated cellulose.

The main functions of the outer layer 52 in the sanitary towel are to guide fluid into the sanitary towel 43, to feel soft and agreeable against the body of the wearer, and to prevent so-called back-wetting, that is to say absorbed bodily fluid forcing back against the skin of the wearer. For reasons of comfort and in order to avoid skin irritation, it is important that the surface on that part of the sanitary towel which bears against the skin of the wearer is kept as dry as possible during use. A dry surface on the sanitary towel moreover feels cooler and more pleasant to the wearer during use, and is more acceptable, both in purely visual terms and during handling of the sanitary towel when the latter is to be changed, than a soiled, wet surface.

The absorption layer 53 is suitably made from cellulose pulp. This may be in the form of rolls, bales or sheets which are dry-defibrated and converted in fluffed form into a pulp mat, sometimes with the addition of so-called superabsorbents which are polymers with the capacity to absorb several times their own weight of water or bodily fluid. Examples of other materials which can be used are various types of natural fibres such as cotton fibres, peat or the like. It is of course also possible to use absorbent synthetic fibres, or mixtures of natural fibres and synthetic fibres. The absorption material can also contain other components, such as dimensionally stabilizing means, liquid-dispersing means, or binders such as, for example, thermoplastic fibres which have been heat-treated in order to hold short fibres and particles together as a coherent unit. It is also possible to use different types of absorbent foam material in the absorption layer.

Along the periphery of the sanitary towel 54, the outer layer 52 and the shaped element 2 are joined by a long, narrow piece of material which has been folded to form a seam 55 around the edge of the sanitary towel at its periphery 54. The material used for the seam 55 is preferably a hydrophobic material so as to prevent side leakage. It is also important that the material used for the seam 55 feels soft and pleasant against the skin of the wearer. An example of a suitable material for the seam 55 is a hydrophobic nonwoven.

The sanitary towel 43 has an essentially elongate shape with a longitudinal direction and a transverse direction and has two long sides 56, 57, two short sides 58, 59, two end portions 47, 48 and a central portion 50 located between the end portions, and also a longitudinal center line 60.

Figure 11A:
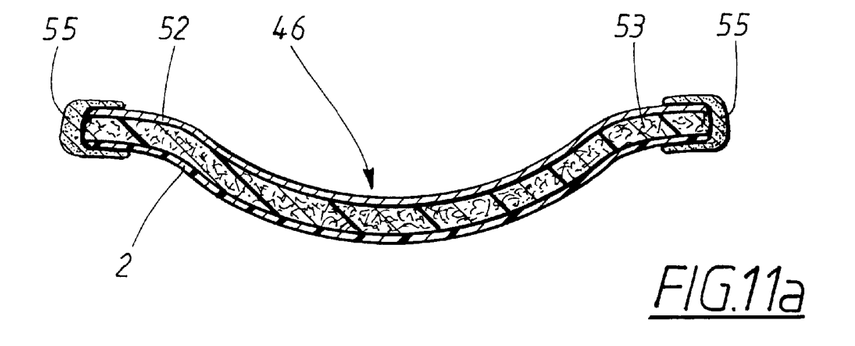
FIG. 11a shows a section along the line X1a–X1a through the sanitary towel in FIG. 10.
Figure 11B:
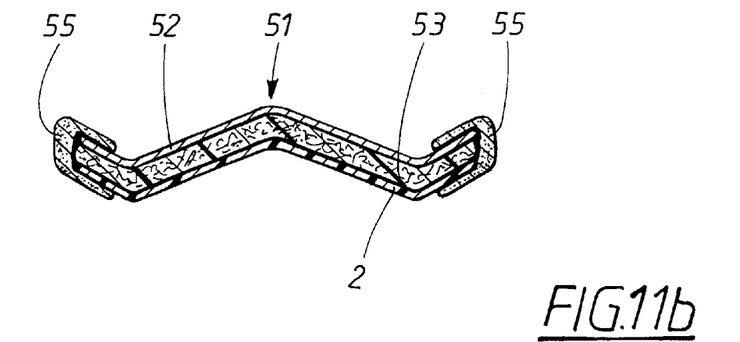
FIG. 11b shows a section along the line X1b–X1b through the sanitary towel in FIG. 10.
Figure 11C:
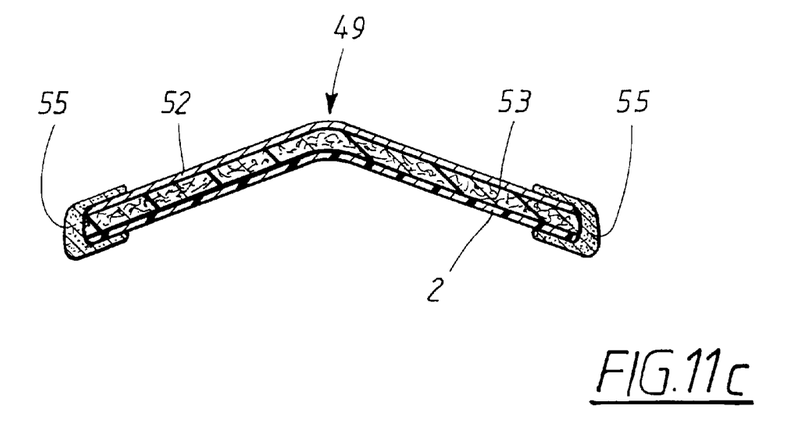
FIG. 11c shows a section along the line X1c–X1c through the sanitary towel in FIG. 10.

FIGS. 11a–11c show a cross section through the sanitary towel 43 in FIG. 10. FIG. 11a shows a cross section through the front end portion 47 of the sanitary towel. The front end portion 47 is the portion which is intended to face forwards on the wearer during use. The front end portion 47 has a bowl-shaped portion 46 which is to fit against the mons pubis of the wearer.

FIG. 11b shows a cross section through the central portion 50 of the sanitary towel. The central portion 50 has a ridge-like raised portion 51 intended to fit against the vestibule of the wearer.

FIG. 11c shows a cross section through the rear end portion 48 of the sanitary towel. The rear end portion 48 has a ridge-like raised portion 49 which is intended to fit against the buttocks of the wearer during use.

It is of course possible to combine the various fold lines shown in the different embodiments freely with one another as long as the purpose of the fold lines, namely that of creating a shape adapted to the body and/or creating leakage barriers, is not compromised. For example, a number of curved fold lines can be arranged along the shaped element. Two or more curved fold lines in the central portion, which are concave in relation to the longitudinal center line, can advantageously be combined with two or more curved fold lines in the rear end portion, which are convex in relation to the longitudinal center line. The front end portion can also have longitudinal fold lines which are convex in relation to the longitudinal center line of the shaped element. Such fold lines allow the shaping of the bowl-shaped portion in the front end portion.

The different embodiments with fold lines can also be combined freely with a shaped element having a continuous raised portion in the central portion and the rear end portion and with a shaped element having a raised portion in the central portion and a raised portion in the end portion separated by a valley.

The shaped element does not have to constitute the liquidtight rear side on the absorbent product according to the invention. A separate liquid-blocking layer made of, for example, polyethylene can constitute the liquidtight rear side of the product. This may be suitable in a case where the shaped element is not liquidtight. The shaped element does not have to lie adjacent to the rear side on the product but may, for example, lie between the outer layer and the absorption layer. In this case, the shaped element can be perforated so as to allow bodily fluid through. A separate liquid-blocking layer is of course then necessary.

The invention is not to be considered as being limited to the embodiments described here, but a number of further variants and modifications are possible within the scope of the patent claims below.

What is claimed is:

1. A method of producing a shaped element, characterized in that a blank, intended to constitute the shaped element, is produced in plane form with an essentially elongate shape with a longitudinal direction and a transverse direction, two short sides and two long sides, two end portions and a central portion, where one end portion is given a width which increases towards the short side of the blank and a cutout is arranged in the other end portion, the blank is folded double along a longitudinal center line of the blank, the cutout is joined together and the joined parts are folded up into a three-dimensional state.

2. A method of producing a shaped element according to claim 1, characterized in that fold indications are arranged in the longitudinal direction of the blank before the cutout is joined together.

3. A method of producing an absorbent product, selected from the group consisting of a sanitary towel, an incontinence pad, and a panty liner, characterized in that a blank intended to constitute a shaped element in the absorbent product is produced in plane form with an essentially elongate shape with a longitudinal direction and a transverse direction, two short sides and two long sides, two end portions and a central portion, where one end portion is given a width which increases towards the short side of the blank and a cutout is made in the other end portion, the blank is folded double along a longitudinal center line of the blank, an absorption layer and then an outer layer are arranged on each surface, after which the side edges along the cutout formed, the absorption layers and also the outer layers are joined and the joined parts are folded up into a plane state.

4. A method of producing an absorbent product according to claim 3, characterized in that two fold indications are arranged essentially in the longitudinal direction of the blank, in at least the central portion of the blank, one on each side of the longitudinal center line.

* * * * *